(12) United States Patent
Claussen et al.

(10) Patent No.: US 8,449,830 B2
(45) Date of Patent: May 28, 2013

(54) MICROFLUIDIC EXTRACTION AND REACTION DEVICE

(75) Inventors: Jan Claussen, Wiesbaden (DE);
Stephan Wittayer, Montabaur (DE);
Susanne Selzer, Monsheim (DE);
Frithjof Von Germar, Münster (DE)

(73) Assignee: Institut fur Mikrotechnik Mainz GmbH, Mainz (DE)

( * ) Notice: Subject to any disclaimer, the term of this patent is extended or adjusted under 35 U.S.C. 154(b) by 41 days.

(21) Appl. No.: 12/998,269

(22) PCT Filed: Sep. 30, 2009

(86) PCT No.: PCT/EP2009/062677
§ 371 (c)(1),
(2), (4) Date: Jun. 7, 2011

(87) PCT Pub. No.: WO2010/037774
PCT Pub. Date: Apr. 8, 2010

(65) Prior Publication Data
US 2011/0236273 A1 Sep. 29, 2011

(30) Foreign Application Priority Data
Oct. 2, 2008 (DE) .......... 10 2008 042 581

(51) Int. Cl.
| | |
|---|---|
| *B01J 19/00* | (2006.01) |
| *B01J 8/00* | (2006.01) |
| *B01L 3/00* | (2006.01) |
| *B01L 3/02* | (2006.01) |
| *B01D 21/00* | (2006.01) |
| *G01N 1/00* | (2006.01) |
| *G01N 1/18* | (2006.01) |

(52) U.S. Cl.
USPC ........... 422/130; 422/129; 422/187; 422/500; 422/501; 422/502; 422/503; 422/504; 422/505; 422/513; 422/527; 422/600; 422/603; 436/174; 436/177; 436/178

(58) Field of Classification Search
USPC ................ 422/50, 500–505, 513, 519, 525, 422/527, 534, 535, 544, 546, 547, 565, 129, 422/130, 187, 600, 603, 549–551; 436/174, 436/177, 178
See application file for complete search history.

(56) References Cited

U.S. PATENT DOCUMENTS
| | | | |
|---|---|---|---|
| 5,998,214 A | 12/1999 | Guirguis | |
| 6,156,281 A * | 12/2000 | Akers et al. | .......... 423/107 |

(Continued)

FOREIGN PATENT DOCUMENTS
| | | | |
|---|---|---|---|
| CN | 1991370 A | * | 7/2007 |
| DE | 44 32 654 A1 | | 3/1996 |

(Continued)

OTHER PUBLICATIONS

Machine translation of CN1991370A, which was published Jul. 4, 2007.*

(Continued)

*Primary Examiner* — Jill Warden
*Assistant Examiner* — Natasha Young
(74) *Attorney, Agent, or Firm* — Hudak, Shunk & Farine Co. LPA

(57) ABSTRACT

A microfluidic arrangement for extracting and optionally processing an extract from a sample and for transferring the extract in flowable form to a microfluidic chip using an extractor with a compressible extraction chamber and at least one opening thereof, a reactor that has a reaction chamber, an inlet opening that communicates with the at least one opening of the extractor, wherein the two openings define a flow path between the chambers, an outlet opening for fluidically connecting to the microfluidic chip and a ventilation opening of the reaction chamber, and having a filter arrangement installed in the flow path between the extractor and the reactor. A lab-on-a-chip system with such a microfluidic arrangement and a microfluidic chip that is rigidly connected to the reactor.

20 Claims, 3 Drawing Sheets

U.S. PATENT DOCUMENTS

| | | | |
|---|---|---|---|
| 6,959,812 B2 * | 11/2005 | Reif et al. | 206/469 |
| 6,992,181 B2 * | 1/2006 | Tooke et al. | 536/25.4 |
| 7,390,463 B2 * | 6/2008 | He et al. | 422/504 |
| 2004/0182788 A1 | 9/2004 | Dorian et al. | |
| 2009/0087884 A1 * | 4/2009 | Beerling et al. | 435/91.2 |

FOREIGN PATENT DOCUMENTS

| | | |
|---|---|---|
| DE | 10 2006 003 532 A1 | 7/2007 |
| DE | 10 2008 002 675 A1 | 12/2009 |
| DE | 10 2008 002 674 B3 | 5/2010 |
| EP | 1 878 498 A1 | 1/2008 |
| WO | WO 02/18902 A1 | 3/2002 |
| WO | WO 2006/029387 A1 | 3/2006 |
| WO | WO 2007/002579 A2 | 1/2007 |
| WO | WO 2009/117212 A1 | 9/2009 |

OTHER PUBLICATIONS

Germar, F., et al., Sample Preparation for the Analysis of Gluten from Foodstuff . . . , 10th Conf. on Miniaturized Sys. For Chem. & Life Sci, Nov. 5-9, 2006, Tokyo, pp. 1522-1524.

* cited by examiner

MICROFLUIDIC EXTRACTION AND REACTION DEVICE

FIELD OF THE INVENTION

The invention concerns a microfluidic arrangement for extracting and optionally processing a flowable extract from a sample and for transferring the extract to a microfluidic chip. Moreover, the invention concerns a lab-on-a-chip system with such a microfluidic chip including the microfluidic arrangement.

BACKGROUND OF THE INVENTION

The invention therefore lies in the technical field of extraction of biochemical or chemical analytes, especially DNA/RNA material, protein, cells and/or bacteria from samples, especially solid sample, such as soil samples, foodstuffs and the like, with subsequent reaction. For example, in the extraction of DNA/RNA from samples, the sample is combined with an extraction buffer in known fashion, mixed, and then filtered. The extract or filtrate is then usually subjected to further processing in a suitable container. This can be a molecular biology process (such as labeling during an immunoassay) or lysis during a DNA assay.

While the further processing of the extract on microfluidic scale is known—and this refers to filtrate amounts of less than 5 milliliters, typically on the order of 1 μl to 1000 μl and especially less than 500 μl—the extraction itself is carried out manually in several steps on a macroscopic or laboratory scale (filtrate amounts in the multiple-digit milliliter to liter range). A particular problem is the transfer of the extracted sample material to the microfluidic chip. In this way, a not inconsiderable loss of sample material can occur, as well as a risk of contamination for the transfer from one vessel to another. Moreover, it is not easy to introduce the extract into the chip without loss of fluidic control. Not least, extraction on a laboratory scale is costly and presupposes large quantities of the starting substances, especially the sample material.

A step in the direction of extraction is an extraction system as is described, for example, in the publication "Sample Preparation for the Analysis of Gluten from Foodstuff in a Modular Chip-Platform" on the occasion of the 10th International Conference on Miniaturized Chemistry and Life Science, from 5 to 9 Nov. 2006 in Tokyo, Japan. This extraction system uses a method based on a peristaltic or constricted tube pump for mixing the sample with an extraction buffer. To separate the undissolved sample components, a centrifuge is used instead of a filter. Efforts to reduce the centrifuging itself to the scale of microfluidic chips are described more closely in DE 10 2006 003 532 A1. The centrifuge is connected at the inlet and outlet side by a fluidic connection piece to a microfluidic chip.

Yet the technical expense of centrifuge extraction is very high. The centrifuge known from the aforementioned publication contains very many individual parts, some of them moving parts, and is therefore expensive, especially for a onetime use. Furthermore, the problems associated with the handling of the sample and the extract have not been solved. The filling of the extractor on the one hand and the transfer of the extracted sample material from the extractor to the centrifuge represent further problems. In this way, a not inconsiderable loss of sample material can occur, along with a risk of contamination during the transfer from one section of the apparatus to the next.

In summary, it can be said that the performance of the extraction due to the aforesaid reasons is at present cost-intensive, time-consuming, and involves a heightened risk of contamination for personnel and surroundings.

The extraction and preparation of a sample in chip format, i.e., in microfluidic amounts, by means of a module which can be directly connected to a microfluidic chip or a microfluidic arrangement is not known at present.

From WO 2006/029387 A1 is known a portable extraction device with a syringe-like arrangement for pipetting and dispensing an analyte, preferably a nucleic acid, to a purification chip. Between the syringe arrangement and the purification chip, a valve to guide the fluid flow and a filter arrangement are hooked up.

From DE 44 32 654 A1 is known a filtration arrangement for preparation of nucleic acids from natural sources with a syringe-like arrangement, by which the disintegration from the nucleic acid is furthered by a filtration arrangement located upstream from the outlet of the syringe arrangement.

A mere miniaturization of known filtration methods, however, would involve further problems. Traditional filter arrangements for sample extraction have the drawback that the filter pores very quickly get clogged, which necessarily places a limit on miniaturization. A large pressure difference during the filtration would moreover lead to a very fast transport of the extract in a connected microfluidic chip, which would jeopardize the fluidic control there. Also, the pressure strength of the usual microfluidic chips would not be able to withstand the pressures occurring during filtration.

The goal of the invention is to overcome the above problems.

SUMMARY OF THE INVENTION

This problem is solved with a microfluidic arrangement for extracting and optionally processing an extract from a sample and for transferring the extract in flowable form to a microfluidic chip with an extractor comprising a compressible extraction chamber and at least one opening thereof, a reactor that comprises a reaction chamber, an inlet opening that communicates with the at least one opening of the extractor, wherein the two openings define a flow path between the chambers, an outlet opening for fluidically connecting to the microfluidic chip and a ventilation opening of the reaction chamber, and a filter arrangement installed in the flow path between the extractor and the reactor. Advantageous modifications of the invention are the subject of the subclaims.

According to the invention, the microfluidic arrangement has an extractor, a reactor communicating with the extractor by a flow path, and a filter arrangement inserted in the flow path between the extractor and the reactor. The extractor, for its part, has a compressible extraction chamber and at least one opening in same. The reactor has a reaction chamber, an inlet opening communicating with the at least one opening of the extractor, while the two openings define a flow path between the chambers, an outlet opening to the fluidic connection with the microfluidic chip, and a ventilation opening of the reaction chamber.

The benefit of the microfluidic arrangement according to the invention is that a small number of components realize the full functionality of an extraction device in combination with a reaction chamber. The extraction occurs in the extraction chamber, in which the sample has previously been placed, along with the extraction buffer. By compressing the extraction chamber volume, the fluid portion of the extract is pressed by virtue of a pressure difference through the filter arrangement. Undissolved solids are held back in the filter arrangement. The liquid phase passes through the filter arrangement and gets into the reaction chamber.

Moreover, it is important to the invention that the reaction chamber is kept at nearly constant pressure by means of the ventilation opening, which creates a connection between the reaction chamber and the surroundings, whereas the pressure rises in the extraction chamber during the compression. This constantly ensures a sufficient pressure difference between the chambers, which prevents a clogging of the filter if the filter arrangement is adequately dimensioned. Moreover, the pressure from the extraction chamber is not introduced via the reaction chamber and its outlet opening into the microfluidic channel system of the chip and therefore does not lead to an uncontrolled flow behavior, especially an undesired outflow of the extract from the outlet opening, preferably situated at the bottom, from the reactor into the chip. Control of the flow in the chip occurs in customary manner by a pressure difference applied elsewhere on the chip (such as by means of pump or syringe) and a suitable valve control. Also, a control by capillary forces is possible in addition or alternatively to the mentioned version based on the decoupling between pressure in the extractor and microfluidic chip.

Preferably, the extractor has a cylinder-piston arrangement which encloses the compressible extraction chamber.

The realization of the compressible extraction chamber by a cylinder-piston arrangement is especially easy in technical respect. Both the cylinder and the piston can be made cheaply from a suitable polymer material by injection molding, hot stamping, or reaction molding.

One embodiment of the cylinder-piston arrangement calls for having the reaction chamber and the extraction chamber configured as continuous, preferably cylindrical cavity or consecutively arranged, preferably cylindrical cavities of the same or different diameter. The filter arrangement in the manner of a partition wall functionally divides the cavity or cavities into the extraction and reaction chambers. A piston, similar to a syringe, is inserted into the cavity of the extraction chamber in order to produce the necessary filtration pressure. The reaction chamber and possibly also the extraction chamber in this embodiment can be flanged as a separate, hollow cylindrical component onto a microfluidic chip or be integrated in it by forming the cavity in a thicker region of the chip. In particular, chip and reactor and possibly extractor will then be formed as a single piece.

Alternatively, the reactor can also be configured as an independent, preferably cylindrical insert or capsule, which is fitted fluid-tight into a segment of the preferably cylindrical cavity. The rest of the cavity forms the extraction chamber. The filter arrangement is formed by the wall segment of the insert or is integrated into this, which borders on the extraction chamber.

For obvious manufacturing technology reasons, the cavities forming the chambers or cylinders and the outer contours forming the piston in the aforementioned embodiments preferably have a cylindrical geometry.

Advantageously, the cylinder of the extractor can move relative to the filter arrangement and the reactor, while the filter arrangement and/or the reactor are at least partly coordinated with the piston or form the latter.

This can be especially well realized if the reactor is configured in the shape of a hollow cylinder, whose outer circumference is at least for one axial segment fitted into the bore of the extractor cylinder. On the inside of the reactor cylinder is formed the reaction chamber, which is spatially bounded off at the end face by the filter arrangement from the extraction chamber, but is not closed fluid-tight. A microfluidic arrangement of this kind can be produced at especially low cost and is therefore especially suited as a disposable device.

The filter arrangement preferably has at least one filter element and a filter holder connected to the reactor and pressing the filter element against the inlet opening of the reactor. The filter holder is firmly connected to the reactor cylinder by form fitting, frictional fitting and/or material connection, for example, by laser welding, gluing or press-fitting. To stabilize the filter element, a filter bracket can be arranged in front of the entry opening of the reactor. If it is also ensured in this way that the filter element rests fluid-tight against the filter holder or is connected to it, one furthermore ensures that the extract on the way to the reaction chamber must pass through the filter element, so that no unwanted particles can get into the reaction chamber.

In order to make the cylinder-piston arrangement in this embodiment fluid-tight to the outside world in easy manner, the filter holder preferably also has a cylindrical outer contour. With corresponding accuracy of fit, the filter holder can be press-fitted into the hollow cylinder of the extractor. Alternatively, a sealing element is arranged between one outer wall of the filter holder and one inner wall of the extractor cylinder. The sealing element can be fashioned as a one-piece sealing lip, given sufficient elasticity of the material of the filter holder, or as a separate sealing ring.

According to one advantageous modification, the extractor has a stirring element enclosed in the extraction chamber.

This can be, e.g., a magnetic stirring rod (also known as a stir bar) or some other stirring element that is operated without contact. Alternatively or additionally, a mixing effect can also be achieved by acoustic means, vibration or convection through heating or cooling, or by a combination of these measures.

The reactor in the form of a hollow cylinder preferably has a flange for fastening to a microfluidic chip.

The lab-on-a-chip system has a microfluidic arrangement of the above described kind with an extractor, a reactor and a filter arrangement and a microfluidic chip firmly connected to the reactor.

By "firmly connected" is meant here, in contrast to the prior art (e.g., a hose connection), a direct physically neighboring arrangement, possibly with a seal in between. The reactor is, for example, flanged to the aforementioned flange, preferably by means of suitable fastening means (such as screws or clamp elements) by form fitting or by material connection (gluing, welding, especially ultrasound welding) directly to the microfluidic chip.

In the integrated lab-on-a-chip system according to the invention, all of the process steps of a chemical or biochemical assay can be imitated, from the preparation of the sample to the extraction or the detection of the analyte, avoiding the numerous costly and often error-prone individual steps that are necessary in laboratory operation. Examples of assays are enzyme linked immunosorbent assays (ELISA) and polymerase chain reaction (PCR).

At least one channel is provided in the microfluidic chip, communicating with the outlet opening of the reactor.

In one advantageous modification, the microfluidic chip has a valve arrangement for optional connecting or separating of the channel(s) communicating with the outlet opening of the reactor with at least one inlet and/or outlet line.

This makes it possible, for example, to introduce one or more different reagents and/or gases in succession or at the same time through the inlet line(s) in the chip into the reaction chamber and/or remove extract through the outlet line(s) in the chip from the reaction chamber for further processing or investigation. Nor can excess pressure or partial vacuum be formed in the reaction chamber by the ventilation opening. A special application is the introducing of air in the reaction chamber for purposes of mixing of the liquid in the reaction through air bubbles. For this purpose, as well as for safe emptying of the reaction chamber, its outlet opening is situated at the lowest point of the reaction chamber.

BRIEF DESCRIPTION OF THE DRAWINGS

Further problems, features and benefits of the invention shall be explained more closely below by means of a sample embodiment with the help of the drawings. There are shown.

DETAILED DESCRIPTION OF THE INVENTION

Figure 1:
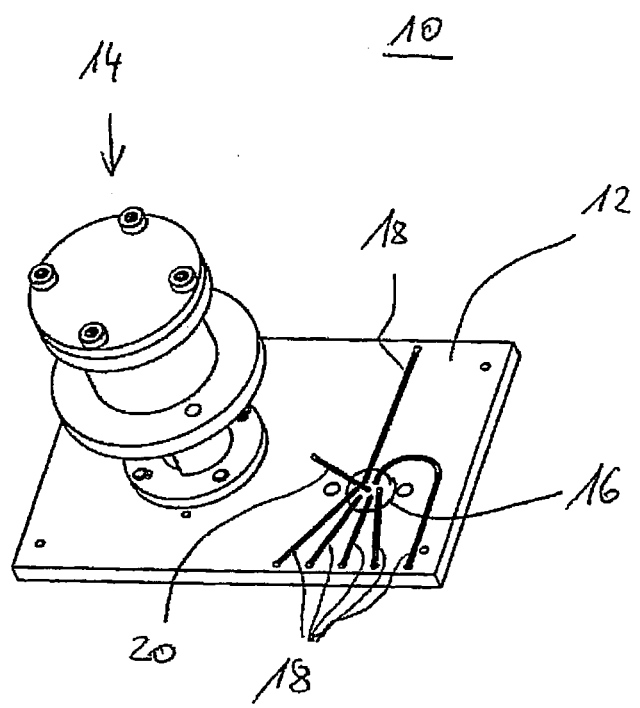
FIG. 1 a perspective representation of one embodiment of the lab-on-a-chip system according to the invention.
Figure 2:
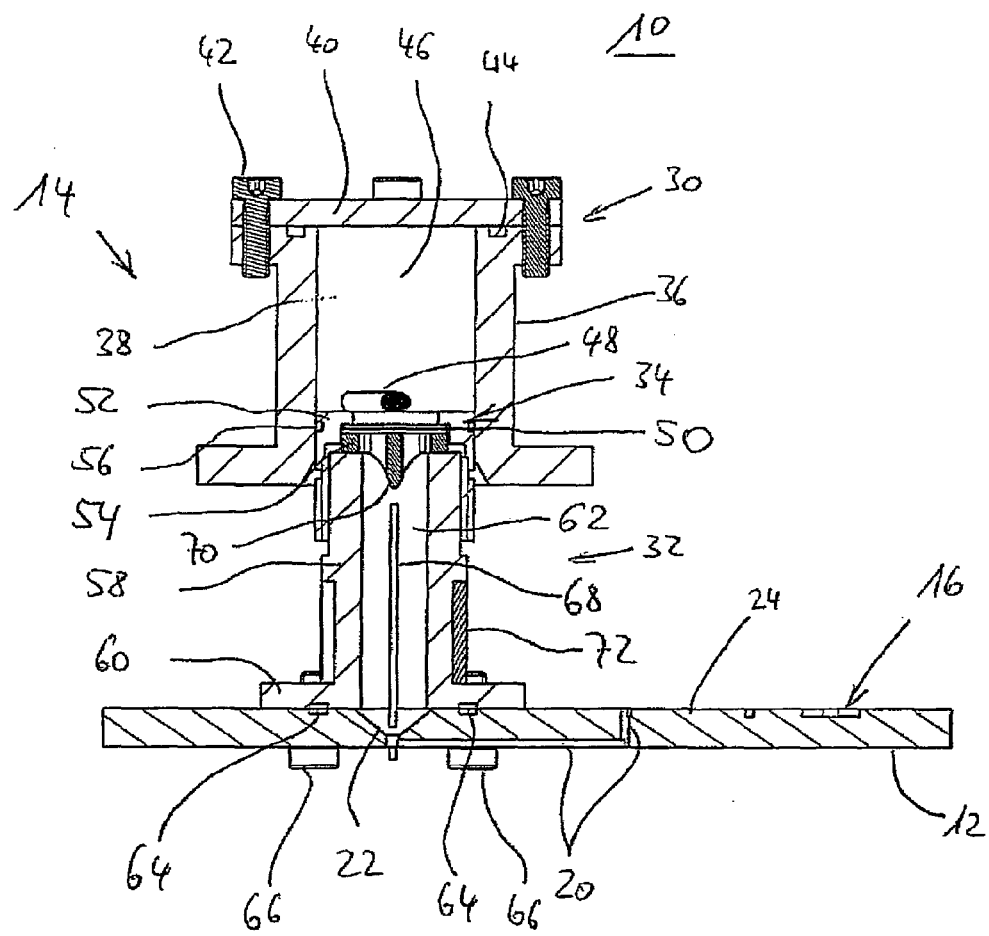
FIG. 2 a sectional view of the lab-on-a-chip system according to FIG. 1.

In FIGS. 1 and 2, the lab-on-a-chip system 10 according to the invention is illustrated by means of one embodiment with a microfluidic chip 12 and a microfluidic arrangement 14 for the extracting and possibly processing of an extract from a sample and for transfer of same in flowable form to the microfluidic chip 12. The microfluidic chip has a valve arrangement 16, which optionally connects one or more inlet and/or outlet lines 18 to a channel 20 or separates them from it. For example, suitable valve arrangements are described in the currently not yet published patent applications DE 10 2008 002 674.3 or DE 10 2008 002 675.1. These have a valve body which can move relative to the chip, which has a sealing surface and defines at least one channel for optional connection and/or separation of fluid lines in the substrate, while the sealing surface of the valve body lies fluid-tight against a sealing surface of the chip. For this, the valve body is pressed against the chip by means of a pressing ring materially connected to the substrate or by means of a clamping element form-fitted to the substrate, while the pressing ring and the clamping element and/or the valve body is at least partly elastic.

The channel 20 emerges into a funnel-like expansion that is open at the top (or drain funnel) 22 in the microfluidic chip 12. The chip 12, in familiar manner, consists of a suitable polymer material and has an essentially rectangular, flat shape similar to a chip card. Suitable plastics are thermoplastics and duroplastics, such as acrylonitrile-butadiene-styrene copolymerizate (ABS), polyoxymethylene (POM), polyether ketones (PEEK), polymethylmethacrylate (PMMA), cyclo-olefin copolymers (COC), cyclical olefin polymers (COP), polycarbonate (PC). The chip 12 is typically a few millimeters thick, while the channel structures are worked into the substrate from the top or bottom side and are sealed by a thin film on the top or bottom side.

On the top side 24 of the chip 12 is found the microfluidic arrangement 14. This has an extractor 30, a reactor 32 and a filter arrangement 34. The extractor 30 has a cylinder-piston arrangement, with parts of the filter arrangement 34 and the reactor 32 forming the piston. The cylinder 36, coordinated with the extractor 30, has a cylinder shell 38 and a cylinder cover 40, which is joined by screws 42 firmly to the cylinder shell 38 and sealed off by a seal 44. The cylinder 36 encloses, at the side opposite the cylinder cover 40, bounded by the piston and more precisely by the filter arrangement 34, a volume, namely, the extraction chamber 46. In the extraction chamber, through the initially opened cylinder cover 40, is placed the sample and an extraction buffer, and the cover 40 is then closed once more. For an easier handling, instead of the cover fixed by the screws 42, a screw-on cover, a snap or click closure, or a glue surface can be used.

In the extraction chamber 46, moreover, there is a stirring element 48 in the form of a magnetic stirring rod for mixing the sample with the extraction buffer. The extraction cylinder 36 can be closed in axial direction relative to the piston, i.e., relative to the filter arrangement 34 and the reactor 32. In this way, the extraction volume 46 can be compressed by pressure from above on the extraction cylinder 36.

The filter arrangement 34 consists basically of one or more filter elements 50, a filter holder 52 and a filter bracket 54. The filter holder has a cylindrical outer contour, in which an annular groove 56 is made to receive a sealing ring. This sealing ring seals off the extraction chamber 46 from the outer world, so that no liquid can escape between the extractor cylinder 36 and the piston.

The reactor 32 consists basically of a hollow cylindrical shell (in short, hollow cylinder) 58 with a one-piece flange 60 arranged at one end. The hollow cylinder 58 has a continuous bore, which forms the reaction chamber 62 with an inlet opening at its top side and an outlet opening at its bottom side. On the bottom side of the flange 60 and correspondingly on the top side 24 of the chip 12 there is an annular groove 64 of the same diameter to receive a sealing ring. Alternatively, the annular groove can be made either only in the flange or only in the chip. The flange 60 if firmly connected to the chip 12 by means of a screw connection 66 and sealed off by means of the sealing ring, so that no liquid can escape from the reaction chamber 62 at this site into the surroundings.

The outlet opening of the reaction chamber 62 is oriented to the funnel-like expansion 22 in the microfluidic chip 12 and thus stands in fluid communication with the channel 20 of the microfluidic chip 12. The upper, open end of the funnel-like expansion 22 has a somewhat larger diameter than the continuous bore of the reaction chamber 62. This ensures that, after the reaction chamber 62 is emptied, no liquid remains behind in dead spaces or corners at the transition from the extractor 32 to the chip 12.

In the reaction chamber 62, moreover, there is a capillary tube 68 arranged eccentrically to the continuous bore. The capillary tube 68 at its bottom side pierces the microfluidic chip 12. It is open at top and bottom, so that it provides a ventilation opening, which connects the volume of the reaction chamber 62 to the surroundings. Optionally, a filter can be provided at one end and/or the other of the tube 68, preventing an escape of germs into the surroundings or, on the contrary, a penetration of contaminants into the extract.

At the upper end face of the reactor cylinder 58 is the filter bracket 54. This carries or supports the filter element(s) 50. The filter holder 52 is fashioned as a sleeve and has an inner threading at its bottom side, which screws together with a corresponding out thread of the reactor cylinder 58. In this way, the filter holder 52 by an inwardly directed ring-shaped edge pushes the filter elements 50 against the filter bracket 54, which in turn is propped against the reactor cylinder 58. In this way, a fluid-tight contact is formed between the ring-shaped edge of the filter holder 52 and the filter element, ensuring that the extract when the extractor cylinder is pressed down can only get through the filter element into the reaction chamber 62, so that no unwanted solids can get past the filter element and into the chamber.

The filter bracket 54 has, at its bottom side in the center, a drip spout 70, where the extract forced through the filter element(s) 50 at first collects before it drips into the reaction chamber 52. This prevents the extract from getting by an undefined path into the extraction chamber 62. In particular, it prevents the extract from closing the ventilation opening of the capillary tube 68.

In the present embodiment, a total of three filter elements 50 are installed. These are specifically uppermost and lowermost a stainless steel filter with a pore size of 200 μm and in between a filter of polyamide with a pore size of 20 μm. The graduating of the pore size of the filter from the larger to the smaller cross section means that in the first filter only the largest particles are held back and sufficiently large continuous openings are formed for smaller particles, which then get caught at the next filter stage. A fouling is largely prevented in this way. The third filter element with, again, larger pore size serves to support the middle, finer filter element. Alternatively or additionally, a filter additive in the form of particles can be used, which like the first coarse filter forms a matrix passable by fine particles and prevents a fouling.

This system enables filtration of samples at high pressures of up to 10 bar. Very good filtration results can be achieved in this way, without the filter element getting clogged. On the other hand, the ventilation makes sure that the fluidic control in the channel system of the microfluidic chip 12 is not lost, despite high pressure.

In a lower axial segment, the reactor tube 58 has a heating cuff 72 arranged on its circumference. This can be used when needed to transform the extract, for example, in a chemical and/or thermal lysis or for acceleration by heating the extract.

Instead of the embodiment shown with flange, chip and reactor can also be fashioned as a single piece. Instead of the screwing of the flange, the connection can also be form fitting by a kind of "quick closure" (click connection) or a material connection (welding or glue connection).

Instead of the orientation shown in the figures, the device can also be intended and designed for overhead operation. In this case, the extractor cylinder can have a solid bottom and be filled from the side of its (single) opening and then be placed onto the reactor cylinder in this orientation from the bottom. The overhead operation under some circumstances already brings about a sedimentation, that is, a separation of the heaviest, largest particles onto the bottom surface of the extractor cylinder. In this way, the filter process can be supported, depending on the application, for example, by a separating of the sample components in the case of soil samples.

Figure 3A:
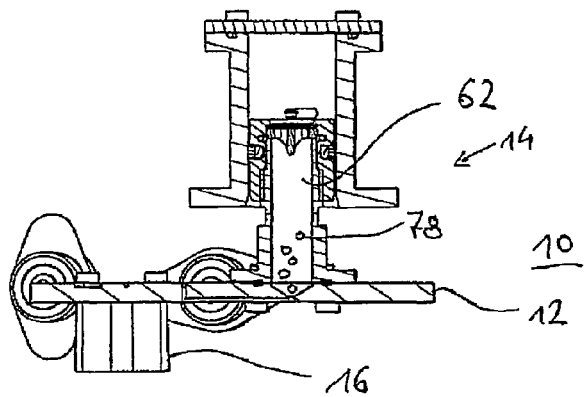
FIG. 3A a sectional side view to illustrate one applications of the lab-on-a-chip system according to the invention and FIG. 3B a top view of the system layout according to FIG. 3A.
Figure 3B:
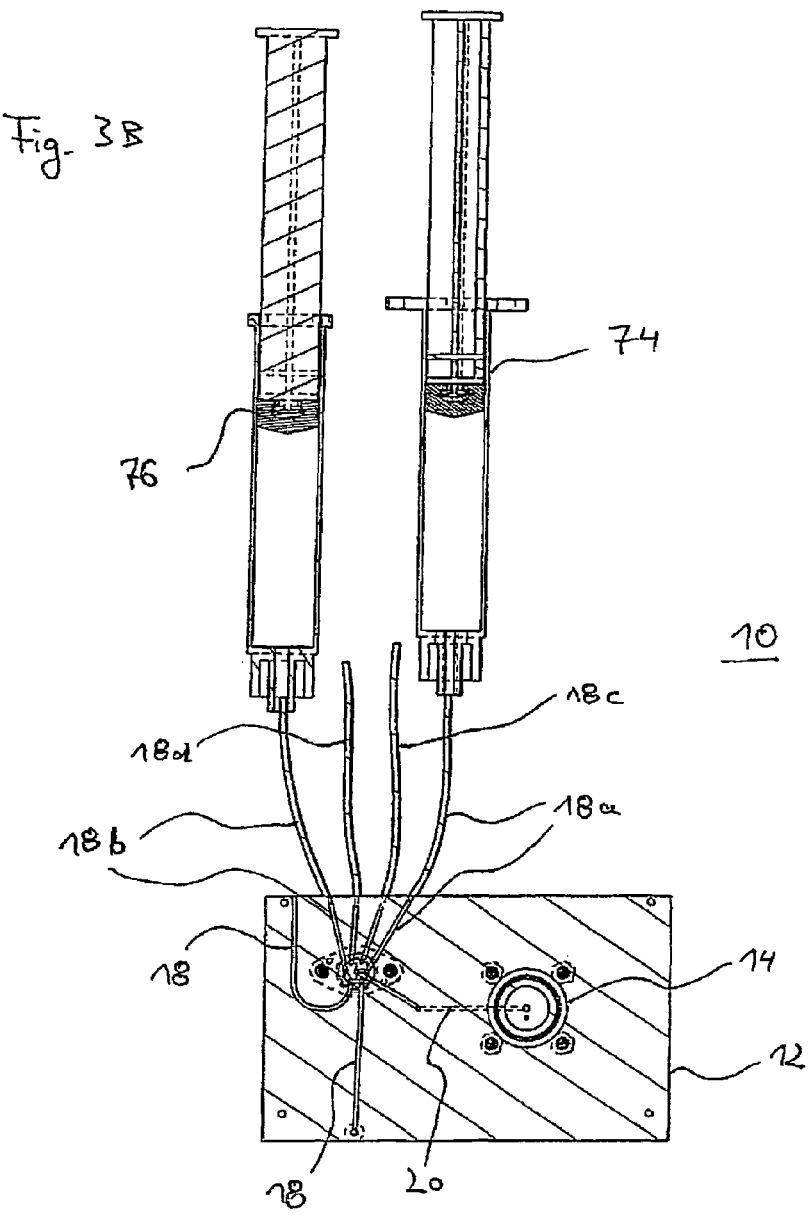

In FIGS. 3A and 3B, a representation of the invented lab-on-a-chip system 10 is shown to illustrate the mode of functioning, especially the introducing of substances into the reaction chamber. As is best seen in the sectional side view of FIG. 3A, the microfluidic arrangement 14 of the invention is situated on the top side of the chip 12. At its bottom side, the housing of the valve arrangement 16 is flanged on. The valve arrangement contains a rotary valve, with a valve body that has at least one channel which can be displaced relative to the chip by rotation for the optional connecting of at least two fluid channels in the chip. In all, 6 inlet and outlet lines 18 and the channel 20 are connected to the rotary valve 16, as can be seen in the top view of FIG. 3B. The inlet and outlet lines 18a, 18b, 18c and 18d within the chip 12 each consist of a channel, which is identical in structure to the channel 20, and outside the chip they consist of a connection piece, in this case, a segment of hose. The other two inlet and outlet lines 18 have no external connection piece. Optionally, by rotating the valve (manually or automatically), the channel 20 can be connected to the end of at least one inlet or outlet line 18.

The chip design and the valve functionality are indicated here only as examples. It is at the discretion of the practitioner to design the valve arrangement for the particular requirement.

As an example, a syringe or pump 74 and 76 respectively are connected to the inlet lines 18a and 18b, more precisely, to the free ends of their hose segments. The syringe 74 in the example shown is filled with air or some other gas. The syringe 76 can be filled with a suitable reagent; for example, in the immunoassay, an antibody bead solution, or in the DNA assay a reagent for the chemical and/or thermal lysis and/or bonding additives. To perform an immunoassay, we first operate the valve in the valve arrangement 16 so that a connection is produced between the inlet line 18b and the channel and, thus, between the syringe 76 and the reaction chamber 62. The solution found in the syringe 76 is injected. After this, the valve arrangement 16 is adjusted so that the gas-filled syringe is connected to the reaction chamber 62. Now, the syringe 74 is activated, so that the gas contained therein is taken through the inlet line 18a and the channel 20 to the reaction chamber 62. At first, the residual solution is emptied from the channel 20 into the reaction chamber 62. Next, the gas emerges there in the form of bubbles 78 from the mouth of the channel 20. The bubbles 78 rise in the extracted liquid in the reaction chamber 62 and serve in particular for the mixing of same; thus, in this example, the mixing of the filtrate with the antibody bead solution.

When the lysis or labeling in the reaction chamber 62 is concluded, the valve arrangement is adjusted so that the end of the channel 20 is connected to the start of another outlet line 18, 18c, 18d. The mixture in the reaction chamber 62 can be taken via the microfluidic path so formed through the microfluidic chip 12, for example, to a connected concentrating and detection module (not shown) or one that is also located on the chip.

The above-described ventilation of the reaction chamber 62 always ensures a controlled fluid transport with very slight pressure differences in the entire process. An experiment has shown that it is possible, thanks to the ventilation capillary, to organize the liquid transport from the reaction chamber to the chip so robustly that no further process control is necessary, such as sensors for detection of the liquid level in the fluid channels at the exit of the extractor.

For explanation of the patent claims, it should be noted that the terms inlet line, outlet line, reactor, extractor, valve arrangement or filter arrangement are to be understood as primarily functional. Structurally, the housing segment forming the reactor and the valve arrangement can be at the same time part of the extractor, namely, the piston, as shown by the sample embodiment. The inlet and outlet lines at least within the chip do not differ structurally from the channel. Functionally, however, they form a connection between the valve and a periphery, while the channel describes the connection segment between the valve and the reaction chamber.

LIST OF REFERENCE NUMBERS

10 Lab-on-a-chip system
12 Microfluidic chip
14 Microfluidic arrangements
16 Valve arrangement
18, 18a, 18b, 18c, 18d Inlet and/or outlet lines
20 Channel
22 Drain funnel
24 Top side
30 Extractor
32 Reactor
34 Filter arrangement
36 Cylinder
38 Cylinder shell
40 Cylinder cover 42 Screws
44 Seal
46 Extraction chamber
48 Stirring element
50 Filter element
52 Filter holder
54 Filter bracket
56 Annular groove
58 Hollow cylinder
60 Flange
62 Reaction chamber
64 Annular groove
66 Screw connection
68 Capillary tube
70 Drip spout
72 Heating cuff
74 Syringe
76 Syringe
78 Bubble

What is claimed is:

1. A microfluidic arrangement for extracting and optionally processing an extract from a sample and for transferring the extract in flowable form to a microfluidic chip, comprising:
an extractor comprising a compressible extraction chamber and at least one opening, wherein the extractor also comprises one or more of a stirring element, an acoustic mixer, a vibration mixer and a convection mixer that utilizes heating or cooling,
a reactor that comprises a reaction chamber, an inlet opening that communicates with the at least one opening of the extractor, wherein the two openings define a flow path between the chambers, an outlet opening for fluidically connecting to the microfluidic chip and a ventilation opening of the reaction chamber, and
a filter arrangement installed in the flow path between the extractor and the reactor.

2. The microfluidic arrangement according to claim 1, wherein the filter arrangement has at least one filter element and a filter holder connected to the reactor and pressing the filter element against the inlet opening of the reactor.

3. The microfluidic arrangement according to claim 1, wherein the extractor has a cylinder-piston arrangement enclosing the compressible extraction chamber.

4. The microfluidic arrangement according to claim 3, wherein the cylinder of the extractor can move relative to the filter arrangement and the reactor and the filter arrangement and/or the reactor are at least partly coordinated with the piston or form the latter.

5. The microfluidic arrangement according to claim 4, wherein the filter arrangement has at least one filter element and a filter holder connected to the reactor and pressing the filter element against the inlet opening of the reactor, and wherein a sealing element is arranged between one outer wall of the filter holder and one inner wall of the cylinder.

6. The microfluidic arrangement according to claim 1, wherein the extractor has the stirring element enclosed in the extraction chamber.

7. The microfluidic arrangement according to claim 1, wherein the reactor is fashioned in the shape of a hollow cylinder.

8. The microfluidic arrangement according to claim 1, wherein the reactor has a flange for fastening to a microfluidic chip.

9. The microfluidic arrangement according to claim 2, wherein the extractor has a cylinder-piston arrangement enclosing the compressible extraction chamber, and wherein the cylinder of the extractor can move relative to the filter arrangement and the reactor and the filter arrangement and/or the reactor are at least partly coordinated with the piston or form the latter.

10. The microfluidic arrangement according to claim 9, wherein a sealing element is arranged between one outer wall of the filter holder and one inner wall of the cylinder; and wherein the extractor has a stirring element enclosed in the extraction chamber.

11. The microfluidic arrangement according to claim 10, wherein the reactor is fashioned in the shape of a hollow cylinder, and wherein the reactor has a flange for fastening to a microfluidic chip.

12. A lab-on-a-chip system comprising: a microfluidic arrangement comprising an extractor comprising a compressible extraction chamber and at least one opening thereof, a reactor that comprises a reaction chamber, an inlet opening that communicates with the at least one opening of the extractor, wherein the two openings define a flow path between the chambers, an outlet opening for fluidically connecting to the microfluidic chip and a ventilation opening of the reaction chamber, and a filter arrangement installed in the flow path between the extractor and the reactor, and
a microfluidic chip that is firmly connected to the reactor.

13. The lab-on-a-chip system according to claim 12, wherein at least one channel in the microfluidic chip communicates with the outlet opening of the reactor.

14. The lab-on-a-chip system according to claim 13, wherein the microfluidic chip has a valve arrangement for an optional connecting or separating of the channel communicating with the outlet opening of the reactor to or from at least one inlet and/or outlet line.

15. The lab-on-a-chip system according to claim 14, wherein the ventilation opening is provided by a capillary tube in the reaction chamber, and wherein a heating device encloses the reactor at least partially.

16. The lab-on-a-chip system according to claim 15, wherein the reactor is an integral component of the microfluidic chip, and wherein the reactor is molded as a single piece onto the microfluidic chip.

17. The lab-on-a-chip system according to claim 12, wherein the ventilation opening is provided by a capillary tube in the reaction chamber.

18. The lab-on-a-chip system according to claim 12, wherein a heating device encloses the reactor at least partially.

19. The lab-on-a-chip system according to claim 12, wherein the reactor is an integral component of the microfluidic chip.

20. The lab-on-a-chip system according to claim 19, wherein the reactor is molded as a single piece onto the microfluidic chip.

* * * * *